United States Patent [19]

Crissman, III et al.

[11] Patent Number: 4,706,368

[45] Date of Patent: Nov. 17, 1987

[54] INFUSION PUMP/CONTROLLER FLOW SENSOR SUPPORT BRACKET

[75] Inventors: John S. Crissman, III, Union Lake; Lyle N. Windingland, Rochester Hills; Natalie A. Kribs, Royal Oak, all of Mich.

[73] Assignee: William Beaumont Hospital, Royal Oak, Mich.

[21] Appl. No.: 820,324

[22] Filed: Jan. 21, 1986

[51] Int. Cl.⁴ .............................................. B23P 19/00
[52] U.S. Cl. .................................. 29/526 R; 248/122; 248/229
[58] Field of Search ............... 248/229, 121, 125, 128, 248/129, 122, 231.7; 29/526 R

[56] References Cited

U.S. PATENT DOCUMENTS

| 371,408 | 10/1887 | Becker | 248/229 |
| 1,262,525 | 4/1918 | Leszczynski | 248/229 X |
| 1,987,826 | 1/1935 | Heumann | 248/229 X |
| 4,211,380 | 7/1980 | Lillegard et al. | 248/229 |
| 4,270,721 | 6/1981 | Mainor, Jr. | 248/231.7 X |

Primary Examiner—J. Franklin Foss
Assistant Examiner—David L. Talbott
Attorney, Agent, or Firm—Harness, Dickey & Pierce

[57] ABSTRACT

This invention relates to a support bracket which positions the flow sensor of an IV pump or controller used in fluid administration systems for patients in medical care. Significant problems have been encountered when the flow sensor and the drop chamber to which it is attached become tilted during use causing improper operation of the system. This invention prevents such problems by securely mounting the IV sensor to the IV pole through the use of a support bracket.

1 Claim, 3 Drawing Figures

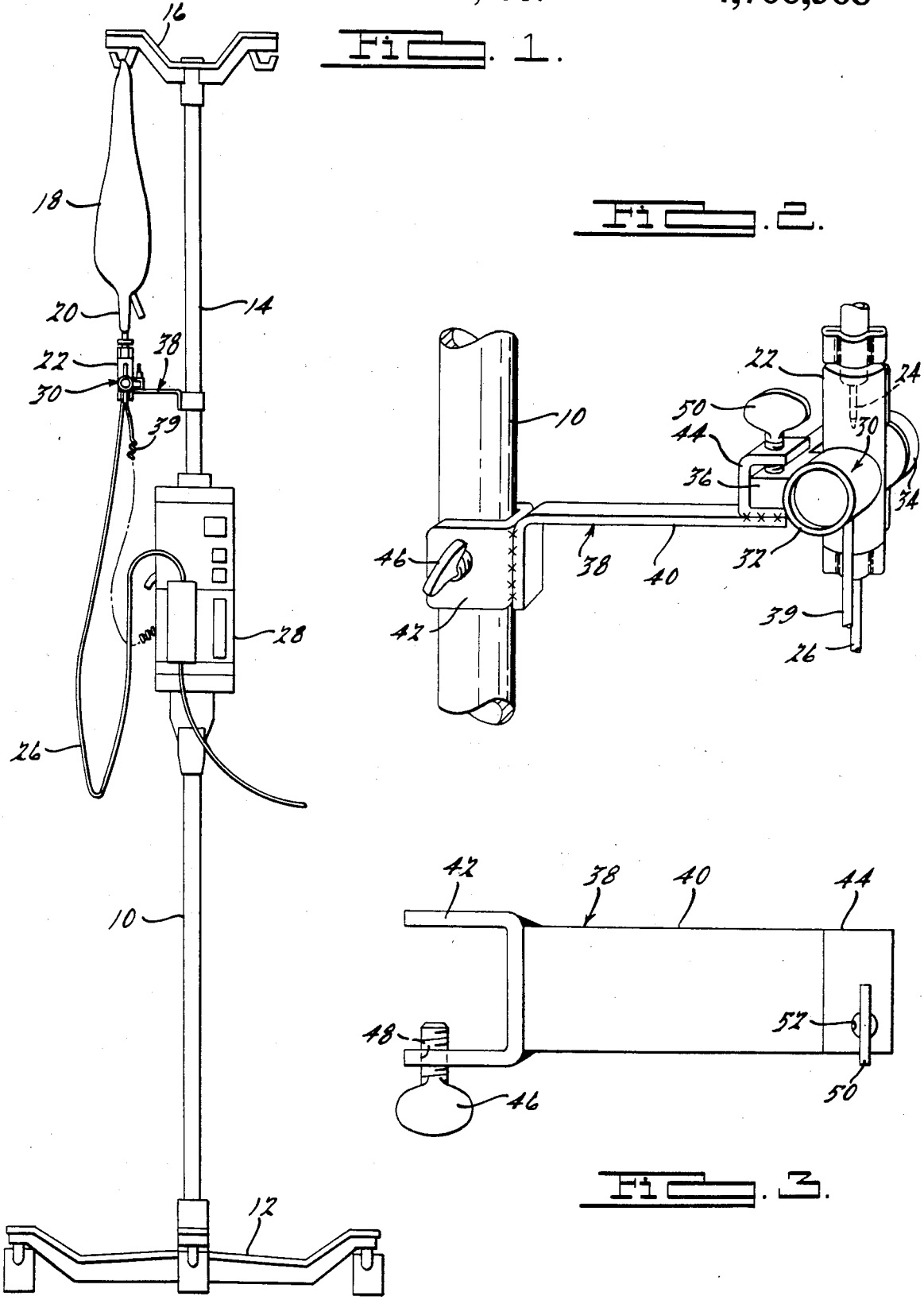

INFUSION PUMP/CONTROLLER FLOW SENSOR SUPPORT BRACKET

BACKGROUND AND SUMMARY OF THE INVENTION

This invention relates to a support bracket and particularly to one adapted to support a flow sensor device used in patient treatment fluid administration systems.

During hospital medical treatment, it is frequently necessary to infuse liquids into a patient intravaneously. Such infusion is normally carried out through the use of a disposable administration bag which is hung from a pole and filled with the desired infusion fluid which is conducted to the patient via a flexible tubing and a hypodermic needle. In certain applications, it is necessary to closely monitor the rate at which the infusion fluids are supplied to the patient. In those instances, rather than merely using gravity or a fixed flow restrictor to control the rate of infusion, an infusion pump or controller is used. An infusion pump typically uses a peristaltic type pumping system which provides fluid to the patient at a controlled rate. Infusion controllers operate as variable restrictors in the adminstration tubing to control the rate of fluid transfer.

Both infusion pumps and controllers are typically mounted to the IV pole and use a remote flow sensor which is attached to an elongated drop chamber connected to the stem of the administration bag. The flow sensor monitors the presence of drops in the drop chamber. The flow sensor causes an alarm to trigger when fluid flow ceases to alert the medical staff that the administration bag has been emptied. The flow sensor typically uses an infrared light interrupter system to monitor the existence of drops in the drop chamber. In order to insure proper operation, it is necessary for the drop chamber attached to the stem of the administration bag to remain in a steady vertical position since sloshing of the liquid in the chamber prevents proper monitoring of the flow conditions.

In practice, while the administration bag normally supports the chamber in a vertical position, there are instances in which external forces act on the drop chamber causing it to become tipped leading to improper operation of the flow sensor. For example, tension on the administration tubing can cause the drop chamber to become tipped. Furthermore, when the entire IV administration system is being moved with the patient, oscillation and swinging of the administration bag and the attached chamber can result. In order to maintain proper operation of the flow sensor, one of the members of the medical staff normally steadies the administration bag by hand when the patient is being moved.

In view of the foregoing, it is an object of this invention to provide a means for securely fixing the position of the administration bag drop chamber and flow sensor in order to prevent false readings and inadvertent activation of the flow alarm.

Additional benefits and advantages of the present invention will become apparent to those skilled in the art to which this invention relates from the subsequent description of the preferred embodiments and the appended claims, taken in conjunction with the accompanying drawings.

BRIEF DESCRIPTION OF THE DRAWINGS

FIG. 1 is a pictorial view of a typical intravaneous administration system, including administration bag, IV pole, infusion pump and flow sensor.

FIG. 2 is an enlarged view of the flow sensor and administration bag stem shown in FIG. 1 and also showing a support bracket in accordance with this invention.

FIG. 3 is a pictorial enlarged view of the support bracket in accordance with this invention.

DETAILED DESCRIPTION OF THE INVENTION

With particular reference to FIG. 1, a number of conventional IV administration components are shown. IV pole 10 is adapted to be connected either to weighted base 12 or to a movable hospital bed. IV pole 10 includes vertical section 14 which supports hook 16. Administration bag 18 is adapted to be hung from hook 16 and includes one or more downwardly extending stems 20. Attached to one of stems 20 is a vertically elongated drop chamber 22. Administration drop set spike 24 is a hollow needle member extending into chamber 22 and attached to stem 20. Drop set spike 24 provides a restricted steady flow of fluid from administration bag 18 into chamber 22. The lower end of chamber 22 communicates with administration tubing 26 which conducts fluid to the patient.

An IV infusion pump or controller 28 controls the flow rate of fluid in administration tubing 26 and is affixed to IV pole vertical section 14. Flow sensor 30, best shown in FIG. 2, includes a pair of generally cylindrical members 32 and 34 connected by support 36. One of the cylindrical members 32 or 34 is biased by a spring such that the unit may be clamped to chamber 22. FLow sensor 30 has pigtail lead 39 connecting to IV pump or controller 28. FLow sensor 30 typically has infrared light transmitters and receivers placed on opposing cylindrical members, thus enabling the sensor to detect the presence of fluid droplets within chamber 22.

Using the above-described devices known to the prior art, no means are provided for securely mounting flow sensor 30 or chamber 22 to insure that the chamber remains in a vertical position. In accordance with this invention, a means for securely positioning chamber 22 is provided to insure proper operation of flow sensor 30. With particular reference to FIGS. 2 and 3, support bracket 38 according to this invention is shown. Support bracket 38 includes an elongated central arm 40 having clamping members 42 and 44 attached at opposing ends, for example, by welding. Clamping member 42 is conformed in a generally "U"-shaped section having threaded thumb screw 46 meshing with threaded bore 48 in one of its legs. Clamping member 42 is dimensioned to engage IV pole 10. Another generally U-shaped clamping member 44 is attached to the opposing end of arm 40. Clamping member 44 also includes thumb screw 50 which meshes with threaded bore 52. Clamping member 44 is adapted to engage support 36 of flow sensor 30.

In use, support bracket 38 is secured to IV pole 10 by loosening thumb screw 46 and then tightening it to firmly engage the pole. Thumb screw 50 of clamping member 44 is loosened to engage support 36 and then tightened to securely clamp the support. When installed, support bracket 38 firmly and securely positions flow sensor 30 and drop chamber 22. With support bracket 38 in use, significant improvements in the operation of flow sensor 30 result. Forces applied on administration tubing 36 or movement imparted to IV pole 10 will not cause tilting of chamber 22. Other embodiments of support bracket 38 within the scope of this invention could employ clamping mechanisms such as deflected spring elements rather than threaded members such as thumb screws 46 and 50.

While the above description constitutes the preferred embodiments of the present invention, it will be appreciated that the invention is susceptible to modification, variation and change without departing from the proper scope and fair meaning of the accompanying claims.

What is claimed is:

1. A method for supporting the drop chamber of an IV fluid administration system having a vertically extending IV pole, an administration bag having said drop chamber attached thereto, and a flow sensor attached to said drop chamber for monitoring the presence of fluid in said drop chamber, comprising the steps of:

providing a vertically extending IV pole, an administration bag associated with said vertically extending IV pole, a drop chamber having a fluid flow path associated with said administration bag, and a flow sensor attached to said drop chamber for monitoring the presence of fluid flow in said drop chamber fluid flow path, providing a rigid support bracket having an elongated arm section, a first clamping member adapted to be removably secured to said IV pole, and a second clamping member adapted to be removably secured to said flow sensor, orientating said first clamping member with respect to said IV pole such that said first clamping member is clamped to said IV pole along a substantially vertical axis, thereby orientating said second clamping member with respect to said first clamping member such that said second clamping member clamps along an axis substantially perpendicular to said first clamping axis, attaching said first clamping member to said IV pole, attaching said second clamping member to said flow sensor such that said drop chamber fluid flow path is substantially parallel to said IV pole, and preventing movement of said first clamping member and said second clamping member with respect to said arm section so that said rigid support bracket, when attached to both said IV pole and said flow sensor, supports said flow sensor and said drop chamber to maintain said drop chamber and fluid flow path in a desired orientation.

* * * * *